(12) United States Patent
Blackwell et al.

(10) Patent No.: US 8,642,678 B2
(45) Date of Patent: Feb. 4, 2014

(54) CARBOXYLIC ACID CONTAINING DISPERSANTS FOR COMPOSITES

(75) Inventors: Gordon B. Blackwell, Constance (DE); Andreas Facher, Constance (DE)

(73) Assignee: DENTSPLY International Inc., York, PA (US)

( * ) Notice: Subject to any disclaimer, the term of this patent is extended or adjusted under 35 U.S.C. 154(b) by 27 days.

(21) Appl. No.: 11/891,891

(22) Filed: Aug. 14, 2007

(65) Prior Publication Data

US 2008/0125515 A1    May 29, 2008

(51) Int. Cl.
*A61K 6/083* (2006.01)
*A61C 5/04* (2006.01)

(52) U.S. Cl.
USPC ........... 523/116; 523/118; 433/228.1; 106/35

(58) Field of Classification Search
USPC ................................ 523/116, 118; 433/228.1
See application file for complete search history.

(56) References Cited

U.S. PATENT DOCUMENTS

| 4,691,045 | A  | * | 9/1987  | Fukuchi et al. | 560/185 |
| 4,913,939 | A  | * | 4/1990  | Montgomery | 427/389 |
| 5,955,514 | A  | * | 9/1999  | Huang et al. | 523/118 |
| 6,191,190 | B1 | * | 2/2001  | Blackwell et al. | 523/115 |
| 6,255,034 | B1 | * | 7/2001  | Shimada et al. | 430/281.1 |
| 2004/0235981 | A1 | * | 11/2004 | Qian | 523/115 |
| 2008/0206715 | A1 | * | 8/2008  | Kawamoto et al. | 433/226 |

* cited by examiner

*Primary Examiner* — Tae H Yoon
(74) *Attorney, Agent, or Firm* — David A. Zdurne; Douglas J. Hura; Leana Levin

(57) ABSTRACT

Polymerizable dental composite comprising a solid filler and an organic polymerizable matrix, said polymerizable matrix comprising:
(i) a polymerizable (meth)acrylic monomer having at least two polymerizable groups and
(ii) from 1.0 to 15 weight-% of a polymerizable monomer having a carboxylic acid group based on the total weight of said polymerizable matrix.

12 Claims, No Drawings

CARBOXYLIC ACID CONTAINING DISPERSANTS FOR COMPOSITES

RELATED APPLICATIONS

This application claims benefit of and priority to International Patent Application Ser. No. PCT/EP2006/001341, filed on Feb. 16, 2006, which claims priority of EP Patent Application Ser. No. 05003049.3 filed on Feb. 14, 2005, now published as EP 1690520 B1, which are herein incorporated by reference for all purposes.

FIELD OF THE INVENTION

This invention relates to a resin-based polymerizable dental composite having a high filler loading. Further, this invention relates to new polymerizable compounds having a carboxylic acid group. Further this invention relates to a method of producing a polymerizable resin-based dental composite. Moreover, the invention relates to a method of preparing a dental restoration and to a dental composite obtained by polymerizing the polymerizable dental composite filling material of the invention.

BACKGROUND TO THE INVENTION

The first polymer based (resin-based) dental filling materials essentially comprised unfilled polymethylmethacrylate. Although these materials showed certain improvements on the filling materials used up to that time, the polymer was soft and exhibited very high wear and shrinkage. A further improvement in properties of the polymer based filling materials was obtained when an inorganic filler was incorporated into the polymer, and this lead to dramatically reduced wear and shrinkage, and generally more favourable physical properties. This class of dental filling material became known as composites. It is now well known that for a cured composite, the surface hardness increases and the degree of shrinkage decreases as the filler content of the composite is increased. A high surface hardness is desirable because this tends to decrease abrasive wear. Shrinkage of a dental filling material on curing has the consequence that the filling pulls away from the tooth surface on curing, and forms a gap between the filling and the tooth. Bacteria and fluids are able to penetrate between the filling and the tooth, which often leads to renewed decay of the tooth. A low shrinkage for a dental filling material is therefore desirable because this reduces the size of the gap formed between the filling material and the tooth, and therefore reduces the propensity for new decay of the tooth. The upper filler content of a composite is however generally limited because with high filler levels the composite material becomes too stiff. In extreme cases it is difficult or impossible to form a homogenous paste, and even if a paste is obtained it may be too stiff to be used. One problem with dental composite filling materials is therefore to obtain pastes with high filler loading, while still retaining a consistency that allows easy use.

The adduct between hydroxypropylmethacrylate and succinic acid has been used to promote adhesion to tooth substance (Dep. Dent. Mater. Dev., Fukuoka Dent. Coll., Fukuoka, 814-01) and was mentioned in patents JP3021603 and JP53051237 as an adhesion promoter to teeth. In WO 97/29732 adducts of 2-hydroxyethylmethacrylate (HEMA) with various anhydrides are mentioned, in particular the adduct of hydroxyethylmethacrylate with glutaric and succinic anhydrides, for dental cements or ionomers. The former adduct is termed GMA in WO 97/29732. However, WO 97/29732 describes water-containing dental cements containing adducts of HEMA with various aryl anhydrides that contain at most 76.85% filler by weight (about 55% filler by volume using an overall density of the metallic filler powder of about 5.5 $g/cm^3$), a level which is easily reached using conventional resin mixtures containing no such adducts. No mention is made of a possibility of obtaining high volume-% filler loadings. WO 97/29732 is not concerned with dental composites nor with the problem of increasing the filler load of dental composites.

The use of dispersing agents to aid incorporation of a filler into a liquid matrix is known. For instance, in U.S. Pat. No. 4,407,984 and EP0053442 it is mentioned that a dispersing agent is desirable to assist in dispersing a filler into a composite material. In U.S. Pat. No. 4,407,984 and EP0053442 dispersing agents based on phosphoric acid esters and alkyl amines are mentioned. U.S. Pat. No. 6,300,390 mentions the use of a phosphate ester dispersing agent. As particularly preferred dispersants are mentioned phosphoric esters containing polymerizable groups, or phosphate esters containing a carboxylic ester group and an ether group. As demonstrated in the examples, such phosphate esters have a very low pH which is deleterious to some dental glasses. The filler load achieved in U.S. Pat. No. 6,300,390 is, however, insufficient and does not provide for high mechanical strength after polymerization. If the filler load in the compositions of U.S. Pat. No. 6,300,390 is increased, the viscosity becomes too high and no homogenous paste can be formed.

It is therefore a problem of the invention to provide a polymerizable dental composite having an increased filler content, while still having a sufficiently low viscosity for easy use. It is another problem of the invention to provide a polymerizable dental composite exhibiting reduced shrinkage upon polymerization while having a good or improved strength after polymerization. It is another problem to provide a polymerizable dental composite having an increased filler load and, good handling properties and giving, upon polymerization, a polymerized dental composite having good physical properties.

DESCRIPTION OF THE INVENTION

This object is achieved by a polymerizable resin-based dental composite comprising a solid filler and an organic polymerizable matrix, said polymerizable matrix comprising:
(i) a polymerizable (meth)acrylic monomer having at least two polymerizable groups and
(ii) from 1.0 to 15 weight-% of a polymerizable monomer having a carboxylic acid group based on the total weight of said polymerizable matrix.

The invention further provides a method of producing a polymerizable resin-based dental composite, comprising blending
(a) a solid filler,
(b) a polymerizable matrix comprising
  (i) a polymerizable (meth)acrylic monomer having at least two polymerizable groups and
  (ii) from 1.0 to 15 weight-% of a polymerizable monomer having a carboxylic acid group based on the total weight of said polymerizable matrix as defined herein; and
(c) a radical polymerization initiator system for thermal or for light curing of said polymerizable dental composite.

The invention further provides a polymerizable dental composite comprising at least 80% by weight of a solid filler based on the weight of said polymerizable dental composite and an organic polymerizable matrix, said polymerizable matrix comprising:
(i) a polymerizable (meth)acrylic monomer having at least two polymerizable groups and
(ii) from 1.0 to 15 weight-% of a polymerizable monomer having a carboxylic acid group based on the total weight of said polymerizable matrix, said polymerizable monomer having a carboxylic acid group is a compound having
   an optionally substituted chain of 6 to 20 atoms selected from carbon, oxygen, and nitrogen,
   a carboxylic acid group at a terminus of said chain, and
   a polymerizable ethylenically unsaturated moiety.

The invention further provides a polymerizable dental composite comprising at least 80% by weight of a solid filler based on the total weight of said polymerizable dental composite and an organic polymerizable matrix, said polymerizable matrix comprising:
(i) a polymerizable (meth)acrylic monomer having at least two polymerizable groups and
(ii) from 1.0 to 15 weight-% of a polymerizable monomer having a carboxylic acid group based on the total weight of said polymerizable matrix, said polymerizable monomer having a carboxylic acid group is a compound having the following formula:

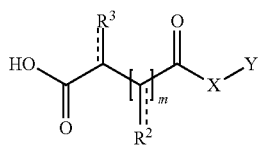

wherein
$R^2$ and $R^3$ are independently H, a $C_{1-6}$ alkyl group or an alkylidene group, whereby the dashed double line indicates a single bond or a double bond;
m is an integer of from 1 to 5, whereby in the case of m being 2 or higher, multiple groups $R^2$ may be identical or different;
X is O or $NR^8$, $R^8$ being hydrogen or an alkyl group; and
Y is a group containing one or more polymerizable ethylenically unsaturated groups.

Said alkylidene group is preferably a $C_{1-6}$ alkylidene group and said alkyl group of $R^3$ is preferably a $C_{1-6}$ alkyl group.

The invention further provides a method of preparing a dental restoration, comprising applying the polymerizable dental composite according to the invention to a tooth to be filled and polymerizing the composite filling material applied to said tooth. Thus, the invention provides use of the polymerizable dental composite of the invention as a tooth filling material. Further, a dental composite obtained or obtainable by polymerizing the polymerizable dental composite of the invention is provided.

Moreover, the invention provides a polymerizable compound wherein the polymerizable carboxylic acid is obtainable by reacting glutaric anhydride with hydroxypropyl (meth)acrylate and/or by reacting glutaric anhydride with glycerol di(meth)acrylate.

The inventors of this invention have surprisingly found that incorporation of a polymerizable monomer having a carboxylic acid group according to the invention into a resin matrix allows the preparation of a polymerizable dental composite having a higher filler load and having a reduced viscosity. Thus, shrinkage of the polymerizable dental composite upon setting is reduced. Further, higher strength and reduced wear of the polymerized dental material is achieved. This is achieved without compromizing other physical properties of the thus produced polymerized composite. Table 2 shows that incorporation of the polymerizable monomer having a carboxylic acid group into the polymerizable matrix achieves pastes with a lower viscosity compared to pastes containing prior art phosphoric acid ester group-containing dispersants of U.S. Pat. No. 6,300,390. Thus, more filler can be incorporated into the polymerizable matrix.

DETAILED DESCRIPTION OF THE INVENTION

The polymerizable dental composite of the invention contains at least a solid filler and an organic polymerizable matrix. Said polymerizable matrix comprises at least said polymerizable (meth)acrylic monomer having at least two polymerizable groups (i) and said polymerizable monomer having a carboxylic acid group (ii). Said polymerizable matrix may contain other polymerizable monomers which may have a polymerizable group, e.g. one polymerizable group (see below). With the exception of said polymerizable monomer (ii), the polymerizable monomers of said polymerizable matrix are preferably hydrophobic.

The polymerizable monomers of the polymerizable dental composite are capable of free-radical polymerization and have at least one ethylenically unsaturated polymerizable group. Said ethylenically unsaturated polymerizable groups are preferably (meth)acrylic groups. Further, the polymerizable dental composite typically contains a radical polymerization initiator system for polymerizing the polymerizable dental composite, whereby the polymerized dental composite of the invention is obtained.

The polymerizable monomer having a carboxylic acid group (in the following sometimes referred to as "polymerizable monomer (ii)" or as "dispersant") provides the polymerizable matrix of the invention with the capability of dispersing a high amount of said solid filler. Said polymerizable monomer (ii) may be one compound or may be a mixture of 2, three, four or more different polymerizable monomers having a carboxylic acid group. Said polymerizable matrix contains between 1.0 and 15 weight-% of said polymerizable monomer (ii). In another embodiment, said polymerizable matrix contains between 2.0 and 12.0 weight-% of said polymerizable monomer (ii). In a further embodiment, said polymerizable matrix contains between 3.0 and 12.0 weight-%, and, in a still further embodiment, between 4.0 and 11.0 weight-%. The best results may be achieved if said polymerizable matrix contains between 5 and 9 weight-%, preferably between 6 and 8 weight-% of said polymerizable monomer (ii). With a content below 1.0 weight-%, no adequate effect of enabling a higher filler load is achieved. At a content above 15 weight-%, no further effect this is obtained and the physical properties of the polymerizable dental composite tend to deteriorate.

Said polymerizable monomer (ii) may have one, two, three or more carboxylic acid groups. Preferably, it has one or two carboxylic acid groups.

In one embodiment, said polymerizable monomer (ii) may be a compound having
   an optionally substituted chain of 6 to 20 atoms selected from carbon, oxygen, and nitrogen,
   a carboxylic acid group at a terminus of said chain, and
   a polymerizable ethylenically unsaturated moiety.

The substituents of said optionally substituted chain may be $C_{1-6}$ alkyl groups, $C_{1-6}$ alkylidene groups or $C_{1-6}$ alkenyl groups, hydroxy groups, or $C_{1-6}$ alkoxy groups. Said polymerizable monomer (ii) has preferably an optionally substituted chain of 6 to 14 atoms selected from carbon, oxygen and nitrogen.

Said polymerizable ethylenically unsaturated moiety may be an olefinic double bond and said polymerizable monomer (ii) may be an unsaturated fatty acid like a linear unsaturated fatty acid having 6 to 20 carbon atoms, preferably 9 to 18 carbon atoms. Examples of such an unsaturated fatty acid are oleic acid, arachidonic acid, cis-4,7,10,13,16,19-docosa-hexaenoic acid, cis-11-eicosenoic acid, elaidic acid, erucic acid, linoleic acid, linolelaidic acid, linolenic acid, myristoleic acid, nervonic acid, palmitoleic acid, petroselinic acid, petroselinic acid, cis-vaccenic acid.

In one embodiment, however, said polymerizable ethylenically unsaturated moiety is a (meth)acrylic group. A (meth)acrylic group may be a (meth)acrylester group or a (meth)acrylamide group. Said polymerizable monomer (ii) is preferably a (meth)acrylic acid ester having a carboxylic acid group or a (meth)acrylic acid amide having a carboxylic acid group. Said carboxylic acid group may be bound to an aliphatic or to an aromatic moiety. Preferably, it is bound to an aliphatic moiety. Examples of polymerizable monomers (ii) having the carboxylic acid group bound to an aromatic moiety are those obtainable by reacting phthalic anhydride with HEMA or 3-hydroxypropyl(meth)acrylate.

In one embodiment, said polymerizable monomer (ii) is a compound of the following formula (1):

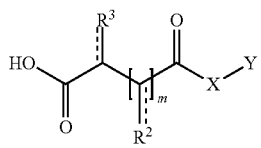

wherein $R^2$ and $R^3$ are independently hydrogen, an alkyl group or an alkylidene group, whereby the dashed double line stands for a single bond or a double bond;
m is an integer of from 1 to 5, whereby in the case of m being 2 or higher, multiple groups $R^2$ may be identical or different;
X is O or $NR^8$, $R^8$ being hydrogen or an alkyl group; and
Y is a group containing one or more polymerizable ethylenically unsaturated groups.

In the above formula (1), the alkyl group and the alkylidene group may be linear or branched, substituted or unsubstituted moieties having 1 to 10 carbon atoms. Preferably, the alkyl groups are $C_{1-6}$ alkyl groups and the alkylidene group is a $C_{1-6}$ alkylidene group. Examples of the optionally substituted $C_{1-6}$ alkyl groups are the following optionally substituted groups: methyl, ethyl, propyl, butyl, pentyl, and hexyl. The examples of the optionally substituted $C_{1-6}$ alkylidene group are the following optionally substituted groups: methylidene, ethylidene, propylidene, butylidene, pentylidene, and hexylidene. The dashed double line in the above formula (1) is a single bond, if $R^2$ or $R^3$ are alkyl groups or H. The dashed double line in the above formula (1) is a double bond, if $R^2$ or $R^3$ are alkylidene groups. Group Y contains at least one polymerizable ethylenically unsaturated moiety as defined above, preferably it contains a (meth)acrylic moiety. The alkyl group of $R^8$ is as defined for $R^2$ and $R^3$.

The dashed double line is preferably a single bond, whereby $R^2$ and $R^3$ may be, independently, a hydrogen atom or an alkyl group as defined in the previous paragraph.

The substituents of said optionally substituted moieties may be $C_{1-6}$ alkyl groups, hydroxy groups, or $C_{1-6}$ alkoxy groups.

In another embodiment, the polymerizable monomer (ii) is a compound of the following formula (2):

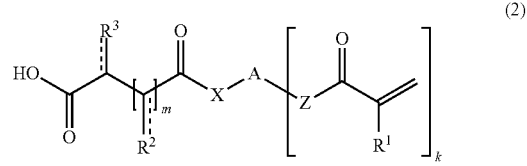

wherein $R^1$ is H or methyl;
A is an optionally substituted alkylene group having 2 to 12 carbon atoms;
$R^2$ and $R^3$ are independently H, an alkyl group or an alkylidene group, whereby the dashed double line stands for a single bond or a double bond;
k is an integer of from 1 to 5;
and m is an integer of from 1 to 5, whereby in the case of m being 2 or higher, multiple groups $R^2$ may be identical or different;
X is O or $NR^8$, $R^8$ being hydrogen or an alkyl group; and
Z stands for an oxygen atom or for $NR^9$, wherein $R^9$ has the same meaning as $R^8$ above.

k may be 1, 2, 3, 4 or 5. Preferably, k is 1, 2 or 3. Most preferably, k is 1.

The alkylene group A is a chain of 2 to 12, preferably 2 to 10, more preferably 3 to 8, and most preferably 3 to 5 carbon atoms and may be substituted. Possible substituents of A are $R^4$, $R^5$, $R^6$, and $R^7$ of formula (3) below. In the case of k being 2 or higher, the moiety in the bracket indexed by k is a substituent of A.

Other residues of formula (2) are as defined for formula (1).

In a further embodiment, said polymerizable monomer (ii) is a compound of the following formula (3):

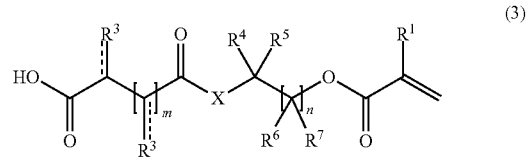

wherein $R^1$, $R^2$ and $R^3$, m, X, and the dashed double lines are as defined above;
$R^4$ and $R^5$ independently are H, an alkyl group, a (meth)acryloyloxyalkyl group, or $R^4$ and $R^5$ may form together an optionally substituted alkylidene group;
$R^6$ and $R^7$ independently are H, an alkyl group, a (meth)acryloyloxyalkyl group, or $R^6$ and $R^7$ may form together an optionally substituted alkylidene group; and
n is an integer of from 0 to 10, whereby in the case of n being 2 or higher, multiple groups $R^6$ or $R^7$ may be identical or different.

The alkyl groups or alkylidene groups of formula (3) correspond to those defined above. The (meth)acryloyloxyalkyl group is preferably a (meth)acryloyloxy-$C_{1-6}$-alkyl group and most preferably a (meth)acryloyloxymethyl group.

In a preferred embodiment of formula (3), m is 1 or 2, n is an integer of from 2 to 5, $R^2$ and $R^3$ are H, at least one of $R^4$ and $R^5$ is H, and at least one of $R^6$ and $R^7$ is H. More preferably, n is 2, 3, or 4, most preferably it is 2. $R^4$ may be a (meth)acryloyloxymethyl group.

Mixtures of two or more different polymerizable monomers (ii) may be used in the polymerizable matrix of the invention. In this case, the content of said mixture of polymerizable monomers (ii) in said polymerizable matrix is as defined above.

Examples of polymerizable monomers (ii) of the invention are obtainable by reacting glutaric anhydride with hydroxypropyl (meth)acrylate and/or by reacting glutaric anhydride with glycerol di(meth)acrylate. Another example of polymerizable monomer (ii) is obtainable by reacting glutaric anhydride with hydroxyethyl (meth)acrylate (HEMA). A further example of polymerizable monomer (ii) is the adduct of glycerol di(meth)acrylate and succinic anhydride or glutaric anhydride.

Preferably, the polymerizable carboxylic acid is obtainable by reacting 1 mol glutaric anhydride with 1 mol hydroxypropyl (meth)acrylate or by reacting 1 mol glutaric anhydride with 1 mol glycerol di(meth)acrylate. Thus, the invention provides compounds of the following formulae or salts thereof:

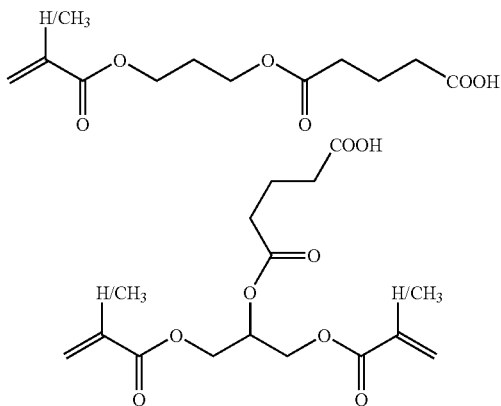

Said polymerizable (meth)acrylic monomer having at least two polymerizable groups (in the following sometimes referred to as "polymerizable monomer (i)") has at least two (i.e. two, three, four or more) polymerizable groups. Such polymerizable monomers are known to the skilled person from conventional dental composites. Examples are di(meth)acrylates of alkanediols and other polyfunctional (meth)acrylates; urethane di(meth)acrylates which may be reaction products of 2 mol of a hydroxyalkyl (meth)acrylate with 1 mol of diisocyanate. Specific examples include 1,3-butylene glycol di(meth)acrylate, 1,6-hexanediol di(meth)acrylate, neopentyl glycol di(meth)acrylate, bisphenol A di(meth)acrylate, bisphenol A glycidyl di(meth)acrylate, ethylene oxide-modified bisphenol A di(meth)acrylate, ethylene oxide-modified bisphenol A glycidyl di(meth)acrylate, 2,2-bis(4-methacryloxypropoxyphenyl)-propane, 7,7,9-trimethyl-4,13-dioxa-3,14-dioxo-5,12-diazahexadecane-1,1,6-diol di(meth)acrylate (UDMA), neopentyl glycol hydroxypivalate di(meth)acrylate, caprolactone-modified neopentyl glycol hydroxypivalate di(meth)acrylate, trimethylolethane di(meth)acrylate, trimethylolpropane di(meth)acrylate, and the like. 2, 3 or more different polymerizable monomers (i) may be used as a mixture.

Examples of polymerizable (meth)acrylic monomers having three polymerizable groups are trimethylolmethane tri(meth)acrylate, trimethylolethane tri(meth)acrylate, trimethylolpropane tri(meth)acrylate, pentaerythritol tri(meth)acrylate, dipentaerythritol tri(meth)acrylate, pentaerythritol tetra(meth)acrylate, dipentaerythritol tetra(meth)acrylate, dipentaerythritol hexa(meth)acrylate, and the like.

Further, the polymerizable matrix of the polymerizable dental composite of the invention may contain other polymerizable monomers like (meth)acrylic monomers having one (meth)acrylic moiety like methyl (meth)acrylate, ethyl (meth)acrylate, n-butyl (meth)acrylate, isobutyl (meth)acrylate, 2-ethylhexyl (meth)acrylate, lauryl (meth)acrylate, tridecyl (meth)acrylate, stearyl (meth)acrylate, cyclohexyl (meth)acrylate, benzyl (meth)acrylate, glycidyl (meth)acrylate, allyl (meth)acrylate, phenoxydiethylene glycol (meth)acrylate, phenoxyhexaethylene glycol (meth)acrylate, dicyclopentenyl (meth)acrylate, isobornyl (meth)acrylate, phenyl (meth)acrylate, caprolactone-modified tetrahydrofurfuryl (meth)acrylate, caprolactone-modified dipentaerythritol (meth)acrylate and caprolactone-modified 2-hydroxyethyl (meth)acrylate.

Additionally, the polymerizable matrix may contain polymerizable monomers having polymerizable ethylenically unsaturated moieties other than (meth)acrylic moieties. These may be 1-alkenes, such as 1-hexene, 1-heptene; branched alkenes, such as vinylcyclohexane, 3,3-dimethyl-1-propene, 3-methyl-1-diisobutylene, 4-methyl-1-pentene; vinyl esters, such as vinyl acetate; styrene, substituted styrenes having an alkyl substituent in the side chain, e.g. alpha-methylstyrene, substituted styrenes having an alkyl substituent on the ring, such as vinyltoluene and p-methylstyrene, halogenated styrenes, such as monochlorostyrenes and dichlorostyrenes; or heterocyclic vinyl compounds, such as 2-vinylpyridine, 3-vinylpyridine, 2-methyl-5-vinylpyridine, 3-ethyl-4-vinylpyridine, 2,3-dimethyl-5-vinylpyridine, vinyl-pyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinylpyrrolidone, N-vinylpyrrolidine, 3-vinylpyrrolidine, N-vinylcaprolactam, N-vinylbutyrolactam, vinyloxolane, vinylfuran; vinyl and isoprenyl ethers; maleic acid derivatives, such as maleic anhydride, methylmaleic anhydride, maleimide, methylmaleimide; and dienes, such as divinylbenzene. The additional monomers may be employed as a mixture. The additional monomers may be used to adjust the mechanical properties of the polymerized filler particles as the case requires.

In the present invention, the polymerizable (meth)acrylic monomer having at least two polymerizable groups (i) and the polymerizable monomer having a carboxylic acid group (ii) are different compounds. The polymerizable matrix of the invention does, in one embodiment, not contain polymerizable monomers carrying carboxylic acid groups other than the polymerizable monomers (ii). The polymerizable matrix of the invention preferably contains at most 20% by weight, more preferably at most 15% by weight, more preferably at most 12% by weight, more preferably at most 11% by weight of polymerizable monomers carrying one or more carboxylic acid groups.

The term "carboxylic acid group" comprises —COOH groups and deprotonated carboxylate groups —COO$^-$. However, the polymerizable monomer(s) (ii) are generally included in the polymerizable matrix with the carboxylic acid groups in protonated form.

The polymerizable matrix of the invention contains at least 50% by weight, preferably at least 60% by weight, more preferably at least 70% by weight of said polymerizable monomer (i). In a highly preferred embodiment, said polymerizable matrix contains at least 80% by weight of said polymerizable monomer (i).

The polymerizable dental composite of the invention contains a solid filler that provides strength to the polymerized dental composite of the invention. The solid filler is a finely divided particulate material. Use of said polymerizable monomer (ii) of the invention allows to incorporate a high amount of said solid filler into said polymerizable matrix of the invention. The polymerizable dental composite of the invention contains at least 50% by weight, preferably at least 60% by weight, more preferably at least 70% by weight, and most preferably at least 80% by weight of said solid filler. Since the filler content expressed as % by weight is not an adequate representation of the filler load said polymerizable matrix can disperse, the filler content should be expressed as volume-%, which makes the numerical value of the filler content independent of the density of said solid filler. Using this definition, the polymerizable dental composite of the invention contain generally at least 55% by volume, preferably at least 60% by volume, more preferably at least 64% by volume, even more preferred at least 66% by volume and most preferably at least 67.5% by volume of said solid filler. Obviously, the exact amount of said solid filler that can be incorporated into said polymerizable matrix depends on the size of the particles of said solid filler, i.e. on the surface area of said solid filler.

Suitable fillers that may be used in the present invention include organic and inorganic solid fillers, whereby inorganic fillers are preferred. Examples of inorganic fillers are glasses e.g. those containing barium, strontium, boron, or zinc, aluminosilicate glass, and metal oxides such as zinc oxide, zirconium oxide, aluminium oxide, silica, apatite, or a cured mixture of resin and filler ground or otherwise reduced in size to a powder. Other examples are fused silica, quartz, crystalline silica, amorphous silica, soda glass beads, glass rods, ceramic oxides, particulate silicate glass, radiopaque glasses (barium and strontium glasses), and synthetic minerals. It is also possible to employ finely divided materials and powdered hydroxyl-apatite, although materials that react with silane coupling agents are preferred. Also available as a filler are colloidal or submicron silicas coated with a polymer. Suitable inorganic fillers are also $La_2O_3$, $ZrO_2$, $BiPO_4$, $CaWO_4$, $BaWO_4$, $SrF_2$, $Bi_2O_3$. Suitable organic fillers include polymer granulates such as polytetrafluoroethylene particles. Small amounts of pigments to allow matching of the composition to various shades of teeth can be included.

The particles of said solid filler should have a mean size below 100 μm, preferably below 50 μm, more preferably below 20 μm. Two or more solid fillers may be mixed that differ in their mean particle size. The particle size distribution may be monomodal or may be polymodal. Preferably, the particle size distribution is bimodal. The particles may be of any desired shape, for instance spherical, irregular as is obtained by mechanical particle size reduction, fibres, whiskers, platelets, dumbbell shaped, or cylindrical, and may be solid, hollow, or porous. Solid fillers that may be used in the present invention are known in the art.

Inorganic fillers are preferably silanated before use in the present invention for rendering the surface of the filler particles more hydrophobic. Silanating agents for this purpose are well known in the art, e.g. 3-methacryloxypropyltrimethoxysilane.

The polymerizable dental composite of the invention further contains a radical polymerization initiator system for thermal curing or for light curing of said polymerizable dental composite. The polymerization initiator is not particularly limited and may be selected from the group consisting of a photoinitiator, a thermal initiator or a combination of a photoinitiator and a thermal initiator. Herein, light curing is preferred. A good light curing initiator system comprises camphorquinone (CQ), dimethylaminobenzoic acid (DMABE), and butylated hydroxytoluene (BHT).

When the polymerizable dental composite of this invention is light cured, it is preferably prepared, stored and delivered to the dentist in a light-tight packing as a one-pack dental material. After having applied the composite to a tooth structure, it may be cured using a conventional dental curing lamp.

The polymerizable dental composite of this invention is essentially free of water. It contains generally below 1 weight-%, preferably below 0.5 weight-%, more preferably below 0.3 weight-%, and most preferably below 0.2 weight-% of water. The polymerizable matrix does preferably not contain more than 1 weight-% poly(meth)acrylic acid. Further, the polymerizable matrix does preferably not contain more than 1 weight-% butane tetracarboxylic acid bis-(2-hydroxyethylmethacrylate) ester.

In one embodiment, the polymerizable dental composite of the invention preferably contains less than 0.5% by weight of water and the polymerizable matrix contains at most 15% by weight of compounds having one or more carboxylic acid groups.

Test Methods

Physical properties of the cured pastes were characterised as far as possible using methods given in the ISO 4049 specification for polymer based dental filling materials. The stiffness of the pastes (the polymerizable dental composites of the invention) was assessed by measuring the force needed to extrude them from small dental syringes known as computes (see U.S. Pat. No. 4,391,590). The pastes were filled into the compules and the force needed to extrude the paste from the compule was measured on a Zwick universal testing machine with a crosshead speed of 28 mm/min and at a temperature of 23° C. The yield strength of the cured pastes was measured in compression using specimens 5 mm high and 4 mm in diameter, and using a Zwick universal testing machine with a crosshead speed of 1 mm/min at a temperature of 23° C. The specimens were made by filling split stainless steel moulds with internal dimensions 5 mm diameter and 4 mm high with the composite paste, pressing the filled mould between glass plates, and curing the samples for 20 seconds from each side using a dental curing lamp having an output of 600 to 800 mW/cm$^2$. The cured specimens were removed from the mould and stored in water at 37° C. for 24 hours before being tested. The yield strength was taken as the force at which the stress-strain relationship became non-linear.

Handling is an empirical property which was assessed by spreading the paste out on a dental pad and observing whether the paste remained as a coherent mass, and also observing how easy it was to form the paste into a shape and whether it retained this shape without slumping. Handling was rated on a scale of 0 to 5, where pastes which were not a coherent mass, were difficult to form, or did not retain their given form where given a low number. Conversely pastes which were coherent, and were easy to form but nevertheless retained their given form were given a high number. The best pastes therefore received a 5 rating on this scale. It is emphasised that it is more important to have a material with an overall balance of good properties, rather than a material in which one or two of the properties are exemplary but others are poor.

Definition of Handling Property Rating:

| handling property | description |
|---|---|
| 1 | Crumbly paste showing dry spots and cracking when spread out on paper. Not acceptable for dentist. |

| handling property | description |
|---|---|
| 2 | Very stiff paste showing cracks when spread out on paper. Not acceptable for dentist. |
| 3 | Stiff but smooth paste, giving cracks in the paste when spread out on paper. Usable clinically. |
| 4 | Smooth and creamy paste but slightly stiffer than ideal. Formation of only a few cracks in the paste when spread on paper. Acceptable for dentist. |
| 5 | Smooth and creamy paste, ideal for dental use. No sign of cracks in the paste when spread out on paper. |

Measurement of Stability of a Paste

The stability of a paste as a measure of the shelf life was measured by filling into dental capsules, then storing these at 60° C. in order to accelerate any changes. At daily intervals, three compules were withdrawn, allowed to cool to room temperature, and the force needed to extrude the paste from the compules was measured using a Zwick universal testing machine with a crosshead speed of 28 mm/min. This speed approximates that at which a dentist would extrude material from a compule in clinical use. The average extrusion force for each of the three compules was plotted against the time in hours after which it was withdrawn for storage at 60° C. The slope of the graph gives the rate in rise of extrusion force in N/h.

Preparation of Carboxylic Acid Acrylic Monomers

SYNTHESIS EXAMPLE 1

HPGM

Glutaric anhydride (22.8 g), hydroxypropylmethacrylate (28.8 g), butylated hydroxytoluene (BHT) (0.05 g), and benzyltriethylammonium chloride (TBAC, 0.05 g) were warmed and stirred in a closed flask to 40° C. until a homogenous liquid was obtained. The temperature was then raised to 100° C. for 9 hours. After this time an FTIR spectrum of the mixture had only a very small peak due to the anhydride, and showed that the anhydride had therefore essentially completely reacted. A colourless clear liquid was obtained and was used without further purification. When applied to moistened pH indicator sticks (Machery-Nagel pH-Fix 0.0-6.0) a pH of 2.5 was indicated.

SYNTHESIS EXAMPLE 2

GGDM

A mixture of glutaric anhydride (22.8 g), glycerine dimethacrylate (46.8 g), BHT (0.05 g), and concentrated $H_2SO_4$ (0.3 g) was warmed to 40° C. for 2 hours then left to stand for 48 hours. After this time no anhydride remained, as shown by FTIR spectroscopy, and a colourless clear liquid was obtained.

In a repeat synthesis, a mixture of glutaric anhydride (22.8 g), glycerine dimethacrylate (46.8 g), BHT (0.05 g), and dimethylaminopyridine (0.07 g) was stirred and heated at 50° for 1 hour then the temperature was raised to 100° C. for 2.5 hours. A colourless clear liquid was obtained which contained only a trace of anhydride. When applied to moistened pH indicator sticks (Machery-Nagel pH-Fix 0.0-6.0) a pH of 2.5 was indicated.

SYNTHESIS EXAMPLE 3

The Adduct of Glutaric Anhydride with Pentaerythritol Triacrylate

Glutaric anhydride (22.8 g), pentaerythritol triacrylate (85% purity, 61.15 g), BHT (0.05 g), and concentrated $H_2SO_4$ (0.15 g) were stirred and heated to 40° C. for 2.5 hours. After this time FTIR showed that all the —OH groups from the pentaerythritol triacrylate (PTA) had been consumed but that unreacted anhydride remained. A further 25.6 g of PTA and 0.15 g concentrated $H_2SO_4$ was added and the mixture left to stand for one day. After further heating to 50° C. for approximately 4 hours a viscous cloudy liquid was obtained.

SYNTHESIS EXAMPLE 4

The Adduct of Glutaric Anhydride with 2-hydroxyethyl Methacrylate (HEMA)

Glutaric anhydride (22.8 g), HEMA (26.13 g), BHT (0.05 g), and TBAC (0.05 g) were put in a closed glass container and stirred and heated at 100° C. for a total of 11 hours. After this time the anhydride had reacted and a clear liquid was obtained. When applied to moistened pH indicator sticks (Machery-Nagel pH-Fix 0.0-6.0) a pH of 2.5 was indicated.

Synthesis of Other Adduct

Other suitable adducts were made analogously to synthesis example 1 by exchanging the glutaric anhydride or hydroxypropylmethacrylate for other suitable anhydrides or radically polymerizable alcohols on a mole for mole basis.

Synthesis of a Dispersant for Comparative Example 2 and 3

The phosphate derivative of caprolactone-2-(methacryloxy)ethyl ester was synthesised according to the method of example given in column 8 of U.S. Pat. No. 6,300,390. The product corresponds to compound 1a of the '390 patent and, of the examples given in the '390 is structurally the closest to the compounds of the present invention, having approximately the same chain length. A clear, light yellow liquid was obtained as described. When applied to moistened pH indicator sticks (Machery-Nagel pH-Fix 0.0-6.0) a pH of 0.0 or lower was indicated. This phosphate dispersant is therefore highly acidic.

EXAMPLES 1 TO 5 AND COMPARATIVE EXAMPLE 1

In a first set of experiments, composite pastes were made in which the resin to glass ratio was varied so that a usable paste was always obtained, and the properties of the resulting pastes were measured. A polymerizable matrix was prepared as follows: a resin mixture was made up from Bis-GMA 2.8 parts, UDMA (7,7,9-trimethyl-4,13-dioxo-3,14-dioxa-5,12-diaza-hexadecan-1,16-diol dimethacrylate) 44 parts, trimethylolpropanetrimethacrylate (TMPTMA) 20 parts, and ethoxylated bis-GMA (EBA) 33.2 parts. HPGM or UDA were added to this resin mixture in the amounts given below, followed by CQ 0.31 parts, DMABE 0.9 parts, and BHT 0.81 parts based on the total resin mixture. This polymerizable matrix (15 parts) was placed in a kneader, and silanated glass filler (e.g. fluoroaluminosilicate glass filler) with a mean particle size of about 5 µm (60 parts) was added. The two were then kneaded together until a homogenous paste was obtained. More glass filler was then added and kneaded into the paste until a suitable consistency and an extrusion force around 80 N to 100 N had been achieved. After a suitable and homogenous paste had been obtained this was kneaded for a further 5 minutes under a vacuum of about 100 mbar to remove air inclusions. The contents of polymerizable matrix and filler contents are given here for convenience in terms of percent or parts by weight. However it is most important to compare formulations by volume % of filler, and in the following tables the weight percents of resin are therefore converted to volume % of filler. The conversion takes the density of the glass to be 3.0 g/cm³, and the density of the polymerizable matrix to be 1.1 g/cm³.

extrusion force was nevertheless higher. Therefore, although the physical properties of example 5 are favourable, HPGM is overall more preferred as a dispersant than GGDM.

EXAMPLES 6 TO 11 AND COMPARATIVE EXAMPLES 2 AND 3

In a second series of experiments the filler content of the paste was held constant at 67.5% by volume (85% filler and

TABLE 1

| Example | dispersant in the matrix | parts dispersant | wt % matrix in paste | Vol.- filler in paste | Extrusion force Newtons | Yield strength. MPa | Surface Vickers hardness | Shrinkage % |
|---|---|---|---|---|---|---|---|---|
| 1 | none | — | 16.6 | 64.8 | 81 | 164.4 | 74.7 | 2.3 |
| comparative example 1 | Undecanoic acid | 1.0 | 15.2 | 67.2 | 72 | 156.8 | 73.9 | 2.1 |
| 2 | HPGM | 3.0 | 14.7 | 68.0 | 102 | 169.6 | 76.5 | 2.0 |
| 3 | HPGM | 5.4 | 14.5 | 68.4 | 75 | 176.5 | 73.2 | 2.0 |
| 4 | HPGM | 6.0 | 14.8 | 67.9 | 96 | 177.0 | 69.6 | 2.0 |
| 5 | GGDM (synthesis example 2) | 3.0 | 15.1 | 67.3 | 141 | 198.9 | 71.6 | 1.7 |

Column "parts dispersant" indicates the parts (by weight) of the dispersant per 100 parts of the resin mixture as defined above. "Paste" is the polymerizable dental composite of the invention. "Matrix" is the polymerizable matrix of the invention.

From Table 1 it is seen that when no dispersing agent was used in the polymerizable matrix, 16.6% by weight polymerizable matrix was needed in the paste (64.8% filler by volume) in order to obtain a paste with an extrusion force around 80 N. However although the surface hardness is good, the yield strength is rather low and the shrinkage is too high. Adding 1% undecanoic acid (UDA) as dispersing agent (comparative example 1) allowed a usable paste to be obtained containing only 15.2% by weight polymerizable matrix (67.17% filler by volume), but although the shrinkage is reduced to 2.1% the yield strength is reduced even further to only 156.8 MPa. Thus, although UDA allows a higher filler content of the paste to be achieved which in turn reduces the shrinkage, the physical properties of the cured paste are adversely affected. Fatty acids as described in U.S. Pat. No. 5,154,613 are therefore not suitable dispersing agents for the present application.

In example 2, HPGM, a polymerizable monomer (ii) according to the present invention, was used in an amount 3% in the resin mixture. A paste could be obtained with a filler content of 68.0% by volume, in which the yield strength was higher than in example 1 which contained no dispersing agent, and the shrinkage was reduced to 2%. When the amount of HPGM was increased to 5.4 parts (example 3), a paste could be made which contained 68.4% filler by volume. The force needed to extrude this from a compule was only 75 N, while the yield strength increased to 176.5 MPa and the shrinkage was reduced to 2.0%. Example 4 with 6 parts HPGM in the resin gave very similar results to example 3. Thus in contrast to UDA, HPGM therefore allows higher filler content of the paste to be obtained leading to reduced shrinkage of the paste on curing, while simultaneously increasing the yield strength. In example 5, the adduct of glutaric anhydride with glycerine dimethacrylate (GGDM) was used as dispersing agent. In example 5 with 3 parts GGDM, a paste could be made containing 67.3% filler by volume (compared to 68 volume % when 3 parts HPGM were used), and although example 5 contained less filler than example 3, the 15% polymerizable matrix by weight). In this second series a different resin mixture was used, leading to slightly higher extrusion forces but lower shrinkage. Thus, a polymerizable matrix of polymerizable acrylate monomers comprising a urethane dimethacrylate resin (UDMA=7,7,9-trimethyl-4,13-dioxo-3,14-dioxa-5,12-diaza-hexadecan-1,16-diol-dimethacrylate), ethoxylated bis-GMA resin (EBA), and the required dispersant was made up. The compositions were chosen so that the ratio of UDMA to EBA was kept essentially constant at about 1:1.3, and only the amount of the dispersant was varied. Camphorquinone 0.3 parts, dimethylaminobenzoic acid 0.9 parts, and BHT 0.6 parts were added as photoinitiators and polymerization inhibitor respectively.

Then, the polymerizable matrix (15 parts) was placed in a kneader, and silanated glass filler with a mean particle size of about 5 μm (85 parts) was added. The two were then kneaded together until either a homogenous paste was obtained, or it became clear that a paste could not be formed. When a homogenous paste was obtained this was kneaded for a further 5 minutes under a vacuum of about 100 mbar to remove air inclusions. Results are shown in Table 2.

When no HPGM was used as in example 6, a homogenous paste could not be obtained with 15% polymerizable matrix, and only a crumbly dry mix was obtained. Physical properties of the paste of example 6 could therefore not be measured. When 3 parts of HPGM were included in the polymerizable matrix in example 7, a homogenous paste could be obtained but the force needed to extrude the paste from the compule was 220±20 Newtons, which is too high for practical use. When 5 parts HPGM were used in Example 8, a homogenous paste was easily obtained and the force needed to extrude the paste from the compule was in a useful range around 130±20 Newtons, however the handling properties were still suboptimal. Increasing the amount of HPGM used above to 5 parts brought no further decrease in extrusion force but still improved the surface hardness and the handling properties of the paste. When 9 parts of HPGM were used in example 11, handling properties of the paste remained good but other properties of the paste became worse.

As a comparative example, a phosphate based dispersant as claimed in U.S. Pat. No. 6,300,390 was used. The compound of comparative example 2 was equivalent to the compound 1a in the '390 patent, and this was chosen as a comparative substance because the overall chain length (15 atoms) is very similar to that of HPGM (13 atoms), and similar properties might be expected. However as shown in table 2, when 3% of compound 1a in the resin was used it was not possible to obtain a homogenous paste. When 7% of compound 1a was used in the polymerizable matrix (1.05% overall in the paste) the paste obtained had an extrusion force of 186 N, and the handling characteristics were very poor.

In these formulations the phosphate based dispersant, compound 1a from U.S. Pat. No. 6,300,390, is therefore inferior to the dispersant of the invention. When methacrylic acid was used in place of the dispersant, a low extrusion force was obtained. However, the handling properties of the paste were poor and it had a strong and unpleasant odour. Further, the shelf life was poor as determined by the rate of the rise of the extrusion force under accelerated aging conditions of 60° C.

From Table 2 it can be seen that the best overall balance of paste properties are obtained when the resin matrix contains between about 6 and 7 parts of HPGM (0.9% HPGM in the polymerizable dental composite). This allows an essentially odourless, stable a paste to be made which has an acceptable extrusion force, and when cured has a high yield strength of 204 MPa and shrinkage of only about 1.7%. This combination of desirable properties could not be obtained when the dispersant of the invention (such as HPGM) was not used.

The content of European patent application No. 05 003 049.3, the priority of which is claimed by the present patent application, is incorporated herein by reference in its entirety.

wherein
$R^2$ and $R^3$ are independently H, a $C_{1-6}$ alkyl group or a $C_{1-6}$ alkylidene group, whereby the dashed double line indicates a single bond or a double bond;

m is 5, whereby multiple groups $R^2$ may be identical or different;

X is O or $NR^8$, $R^8$ being hydrogen or an alkyl group; and

Y is a group containing one or more polymerizable ethylenically unsaturated groups.

2. The polymerizable dental composite of claim 1, wherein said polymerizable matrix includes at least 60% by weight of said polymerizable (meth)acrylic monomer having said at least two polymerizable groups and not containing said carboxylic acid group.

3. The polymerizable dental composite of claim 1, further containing a radical polymerization initiator system for thermal or for light curing of said dental composite.

4. The polymerizable dental composite of claim 1, further comprising: a) less than 1.0% by weight of water.

5. The polymerizable dental composite of claim 1, wherein the solid filler is present in an amount of at least 80 wt % of the dental composite.

6. A method of producing a polymerizable dental composite, comprising blending

TABLE 2

| | | Physical properties of pastes containing 67.5% filler by volume | | | | | |
|---|---|---|---|---|---|---|---|
| Example | Dispersant | % Dispersant in resin | Handling rating | Extrusion force Newtons | Yield strength MPa | Surface Vickers hardness | Shrinkage % | rate of rise in extrusion force at 60° C. |
| 6 | none | 0.0 | 0 | homogenous paste was not formed | — | — | — | |
| 7 | HPGM | 3.0 | 1 | 220.8 ± 20 | 196.8 | 53.6 | 1.76 | |
| 8 | HPGM | 5.0 | 2 | 129.1 ± 20 | 197.6 | 62.9 | 1.75 | |
| 9 | HPGM | 6.0 | 4 | 136.7 ± 20 | 200.8 | 67.0 | 1.67 | |
| 10 | HPGM | 7.0 | 5 | 135.0 ± 20 | 204.7 | 69.2 | 1.72 | 0.02 |
| 11 | HPGM | 9.0 | 5 | 134.6 ± 20 | 197.8 | 67.4 | 1.79 | |
| comp. example 2 | 1a from U.S. Pat. No. 6,300,390 | 3.0 | — | homogenous paste was not formed | — | — | — | |
| comp. example 3 | 1a from U.S. Pat. No. 6,300,390 | 7.0 | 2 | 186 ± 20 | | | | |
| comp. example 4 | methacrylic acid | 7.0 | 2 | 130 ± 20 | | | 2.01 | 0.14 |

The invention claimed is:

1. A polymerizable dental composite comprising at least 50 weight-% solid filler and an organic polymerizable matrix, said polymerizable matrix comprising:
(i) at least one polymerizable (meth)acrylic monomer having at least two polymerizable groups and not containing a carboxylic acid group; and
(ii) a dispersant including at least one polymerizable monomer having a single carboxylic acid group, said polymerizable monomer having said single carboxylic acid group is a compound of the following formula:

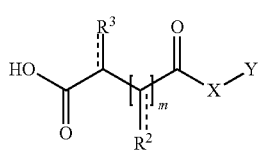

(a) at least 50 wt % solid filler,
(b) a polymerizable matrix comprising
(i) at least one polymerizable (meth)acrylic monomer having at least two polymerizable groups and not containing a carboxylic acid group, and
(ii) a dispersant including at least one polymerizable monomer having a single carboxylic acid group, said polymerizable monomer having said single carboxylic acid group is a compound of the following formula:

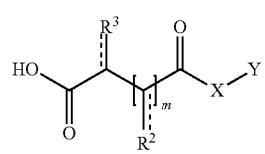

wherein

R² and R³ are independently H, a $C_{1-6}$ alkyl group or a $C_{1-6}$ alkylidene group, whereby the dashed double line indicates a single bond or a double bond;

m is 5, whereby multiple groups R² may be identical or different;

X is O or NR⁸, R⁸ being hydrogen or an alkyl group; and

Y is a group containing one or more polymerizable ethylenically unsaturated groups; and (c) a radical polymerization initiator system for thermal or for light curing of said polymerizable dental composite.

7. The method of claim 6, further comprising the steps of applying the polymerizable dental composite to a tooth and polymerizing the polymerizable dental composite applied to said tooth.

8. The method of claim 6, wherein said polymerizable matrix includes at least 60% by weight of said polymerizable (meth)acrylic monomer having said at least two polymerizable groups and not containing said carboxylic acid group.

9. The method of claim 7, wherein said polymerizable matrix includes at least 60% by weight of said polymerizable (meth)acrylic monomer having said at least two polymerizable groups and not containing said carboxylic acid group.

10. The method of claim 6, wherein the solid filler is present in an amount of at least 80 wt % of the dental composite.

11. A method of producing a polymerizable dental composite, comprising blending (a) at least 50 wt % solid filler, (b) a polymerizable matrix comprising
  (i) at least one polymerizable (meth)acrylic monomer having at least two polymerizable groups, and
  (ii) a dispersant including at least one polymerizable monomer having a carboxylic acid group, a single carboxylic acid group, said polymerizable monomer having said single carboxylic acid group is a compound of the following formula:

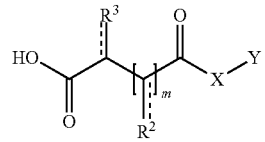

wherein

R² and R³ are independently H, a $C_{1-6}$ alkyl group or a $C_{1-6}$ alkylidene group, whereby the dashed double line indicates a single bond or a double bond;

m is 5, whereby multiple groups R² may be identical or different;

X is O or NR⁸, R⁸ being hydrogen or an alkyl group; and

Y is a group containing one or more polymerizable ethylenically unsaturated groups.

12. The method of claim 11, wherein the at least one polymerizable (meth)acrylic monomer having at least two polymerizable groups does not contain a carboxylic acid group.

\* \* \* \* \*